United States Patent [19]

Biswas

[11] Patent Number: 4,766,067

[45] Date of Patent: Aug. 23, 1988

[54] GENE AMPLIFICATION

[75] Inventor: Debajit K. Biswas, Newton, Mass.

[73] Assignee: President and Fellows of Harvard College, Cambridge, Mass.

[21] Appl. No.: 739,982

[22] Filed: May 31, 1985

[51] Int. Cl.$^4$ .................. C12P 21/00; C12P 19/34; C12N 5/00; C12N 15/00; C12N 1/00; C07H 21/04

[52] U.S. Cl. ........................................ 435/68; 435/91; 435/240.1; 435/240.2; 435/172.1; 435/172.3; 435/243; 435/320; 536/27; 935/6; 935/34; 935/42; 935/43; 935/61; 935/70

[58] Field of Search ................... 435/68, 70, 71, 91, 435/172.1, 172.3, 240, 241, 317, 240.1, 240.2, 317.1, 320; 536/27; 935/6, 34, 42, 43, 61, 70

[56] References Cited

U.S. PATENT DOCUMENTS 4,656,134 4/1987 Ringold ................................ 435/91

OTHER PUBLICATIONS

Ringold et al, J. Molec. Appl. Genet. 1: 165 (1981).
D. K. Biswas et al., "Bromodeoxyuridine Induced Amplification of Prolactin Gene in GH Cells", *Advances in Gene Technology*, Proceedings of the 19th Miami Winter Symposium, Feb. 1987.
D. J. Wilson et al., "Bromodeoxyuridine-Induced Amplification of Prolactin Gene in a GH Subclone," Abstracts 22nd Annual Meeting American Society for Microbiology.
D. K. Biswas et al., "Bromodeoxyuridine Induced Amplification of Prolactin Gene in GH Cells is an Extrachromosomal Event", 74th Annual Meeting of Biological Chemists, Jun. 1983, *Federation Proceedings*.
Stark and Wahl (1984) Gene Amplification, Ann. Rev. Biochem. 53:447–491.
Schimke et al. (1978) Science 202:1051–1055.
Wahl et al. (1979) J. Biol. Chem. 254:8679–8689.
Biswas and Hanes (1982) Nucleic Acid Res. 10:3995–4008.
Biswas et al. (1977) Cell 11:431–439.
Wilson et al. (1983) DNA 2:237–242.
*Harvard Medical Area Focus*, Jan. 12, 1984, pp. 1, 7 and 8.
Chien and Thompson (1980) Proc. Natl. Acad. Sci. USA 77:4583–4587.
Enquist et al. (1979) Gene 7:335–342.
Biswas et al. (1984) Science 219:941–943.

*Primary Examiner*—James Martinell

[57] ABSTRACT

Hybrid DNA capable of effecting controlled amplification in a host cell of a heterologous gene that determines a specific function. The hybrid DNA has the following three different regions of DNA: (1) an "amplicon" that is inducible by an external stimulus; (2) the heterologous gene (or a site for its insertion); and (3) a selectable marker enabling isolation of the transformed host cells. In order to make a desired compound coded by the heterologous gene, a vehicle including the hybrid DNA is introduced into a host cell is transformed with the vector, transformed host cells are grown to a desired population, the external stimulus is controlled to effect amplification of the gene in members of the population, cells containing amplified gene are cultured, and the compound is recovered.

11 Claims, 1 Drawing Sheet

GENE AMPLIFICATION

BACKGROUND OF THE INVENTION

The invention described in this application was made at least in part with the support of funds from the National Cancer Institute (Grant No. CA28218) and the National Heart, Lung and Blood Institute (Grant No. 32034). The U.S. Government may have rights in this invention.

This invention relates to amplification of a gene and enhancing production of a desired gene product.

Organisms use gene amplification, i.e., increasing the number of copies of a specific gene sequence, as a cellular regulatory mechanism used occasionally to overproduce a particular gene product in the normal course of their growth and development or to respond to certain drugs or disease states [Stark and Wahl (1984) Gene amplification. Ann. Rev. Biochem. 53:447–491]. Amplification of specific genes can enable an organism to resist the lethal effects of several toxic substances [Schimke et al (1978) Science 202:1051–1055; Wahl et al (1979) J. Biol. Chem. 254:8679–8689].

Biswas and Hanes [(1982) Nucleic Acid Res. 10: 3995–4008] disclose that the thymidine analog 5-bromodeoxyuridine (BrdUrd) induces amplification of the gene encoding the hormone prolactin (PRL) in a clonal strain of the rat pituitary tumor cell line designated "$GH_1 2C_1$" that does not normally produce PRL, that is, the cell line is ordinarily PRL$^-$. BrdUrd-induced gene amplification is accompanied by PRL synthesis in the PRL$^-$ GH strain [Biswas et al (1977) Cell 11:431–439]. A specific length of DNA (about 20kb), including all of the rat prolactin gene sequence plus about 3kb upstream from the 5' end thereof and about 7kb downstream from the 3' end thereof, is amplified by BrdUrd. The BrdUrd-induced PRL$^+$ phenotype reverts to PRL$^-$ upon withdrawal of the drug [Wilson et al. (1983) DNA 2:237–242].

Harvard Medical Area Focus, Jan. 12, 1984 reports that Dr. Biswas and colleagues have derived a strain of rat pituitary cells which produce prolactin only upon exposure to 5-bromodeoxyuridine (BrdUrd), accompanied by a 50 to 100 fold increase in the gene encoding prolactin. This gene amplification is reported to be reversible upon withdrawal of BrdUrd. The report says,:

"The precise mechanisms of gene amplification in higher organisms are still unresolved . . . 'The trick is in getting hold of the DNA sequence that carries the information for responding to the drug,' [Dr. Biswas] said. 'If we can isolate it and put it in close association with other genes, it is possible that we might be able to amplify those genes.'"

The article further discloses that a viral gene was joined to a DNA segment which included part of the prolactin gene from a BrdUrd-inducible rat cell and a region adjacent to that gene. The viral gene is amplified by BrdUrd.

Chien and Thompson [(1980) Proc. Nat. Acad. Sci. U.S.A. 77:4583–4587] report making overlapping cDNA clones of the rat prolactin gene.

Enquist et al. (1979) Gene 7:335–342 disclose the use of the herpes simplex virus themidine kinase gene as a selectable marker in an E. coli plasmid.

SUMMARY OF THE INVENTION

The invention features a hybrid DNA capable of effecting controlled amplification in a host cell of a heterologous gene that determines a specific function. The hybrid DNA has the following three different DNA regions: (1) an "amplicon" that is inducible by an external stimulus; (2) the heterologous gene (or a site for its insertion); and (3) a selectable marker enabling isolation of the transformed host cells. As used in this patent application, the term amplicon means a DNA segment that effects an increase in the number of copies of at least one other DNA sequence associated with the amplicon. A heterologous gene is a gene that does not naturally occur in association with the amplicon so as to be amplified by it. In order to make a desired compound coded by the heterologous gene: a vehicle including the hybrid DNA is introduced, e.g. by transfection into a host cell; host cells are grown to a desired population; the external stimulus is controlled to effect amplification of the gene in members of the population; cells containing amplified gene are cultured, and the compound is recovered.

In preferred embodiments, the external stimulus is 5-bromodeoxyuridine; the amplicon is derived from DNA associated with a rat prolactin gene, and specifically from DNA substantially similar to (or identical to) a segment of the 10.3 kb at the 5' end of a rat prolactin gene. The heterologous gene codes for human growth hormone, and the host cell is a eucaryotic (most preferably a mammalian) cell.

Other features and advantages of the invention will be apparent from the following description of the preferred embodiment and from the claims.

DESCRIPTION OF THE PREFERRED EMBODIMENT

Brief Description of the Drawing

I. Drawings

II. The Hybrid DNA

Figure 1:
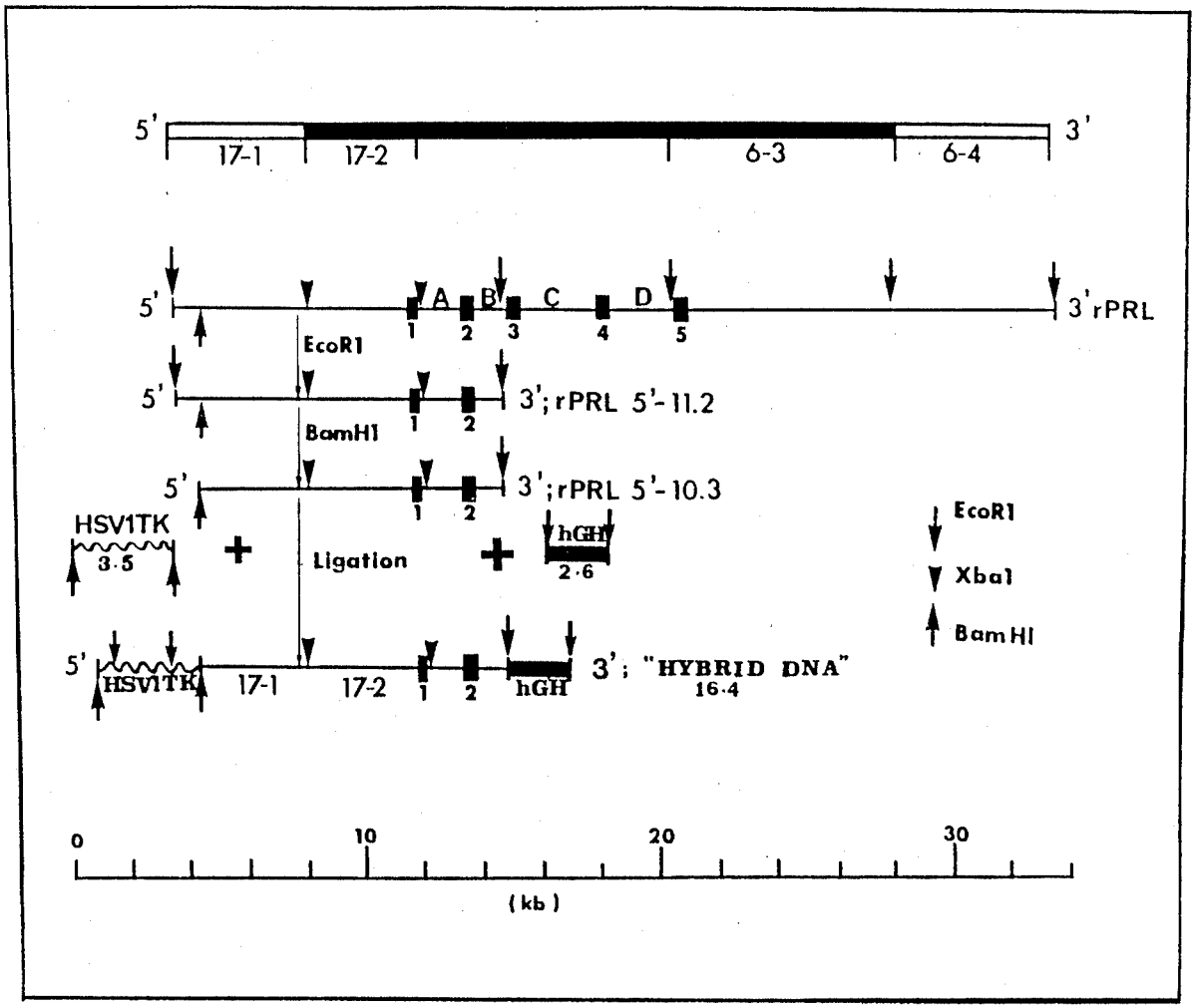
FIG. 1 is a diagrammatic representation of a hybrid DNA sequence.

FIG. 1 is a diagram of a hybrid DNA sequence that contains the amplicon. Specifically, the hybrid DNA sequence includes (reading 5' to 3'): (1) a marker gene, in this case a 3.5 kb gene coding for thymidine kinase which enables transformants to grow in a HAT selection medium; (2) an amplicon, in this case the amplicon is contained within a 10.3 kb sequence from the 5' end of the rPRL gene of a GH cell line; and (3) a 2.6 kb human growth hormone (hGH) gene sequence that is representative of the heterologous gene coding for a desired protein.

An important element of the hybrid for purposes of this invention is the amplicon portion of the 10.3 kb rPRL-related sequence. The amplicon is capable of controlled amplification of gene sequences that are adjacent either to its 5' or its 3' end. While the entire 10.3 kb DNA segment is used in the hybrid DNA described here, amplicon function may reside in a shorter sub-segment within that 10.3 kb seqment, and, in that case, one skilled in the art will readily perceive that the 10.3 kb segment can be divided into restriction fragments that can be tested for amplicon activity and redivided and retested to provide smaller sub-fragments retaining the activity. The invention covers constructions and methods using such sub-fragments.

While the specific embodiment includes a specific marker gene and a specific heterologous gene, the invention covers other markers (e.g., antibiotic resistance) and other heterologous genes.

Applicant has deposited with the American Type Culture Collection in Rockville, MD, a virus comprising the above-described amplicon portion of the rPRL-related sequence. The deposit has been given accession number ATCC 40187. Applicant's assignee acknowledges its responsibility to replace this deposit should the deposit become non-viable before the end of the term of a patent issued hereon, and its responsibility to notify the ATCC of the issuance of such a patent, at which time the deposits will be made available to the public. Until that time the deposits will be made available to the Commissioner of Patents under the terms of 37 CFR §1.14 and 35 USC §112.

A suitable amplicon for use in hybrid DNA can be obtained by digesting the lambda DNA from the deposit with EcoRI and separating the resulting fragments on a 1% agarose electrophoresis gel. In addition to the lambda DNA, the gel will reveal three primary brands representing the rPRL-related sequence: at about 2.0 kb, 4.4 kb, and 11.0 kb. The 11.0 kb segment represents a suitable amplicon.

Alternatively, the hybrid DNA can be constructed as described below and illustrated in FIG. 1 from the elements A-C below.

A. Thymidine Kinase

A thymidine kinase gene from any of a number of known sources can be used. For example, a plasmid containing a herpes simplex type I thymidine kinase gene (HSV1Tk) can be obtained by the technique generally described by Enguist et al. (1979) Gene 7:335–340. The HSV1Tk gene is recovered by digesting the plasmid with a suitable restriction enzyme (e.g. BamH1) and then performing various isolation techniques, such as described in Wilson et al. (1983) DNA 2:237–242.

B. The Amplicon

The amplicon is contained in a 10.3 kb sequence 5′ to the rPRL gene of a PRL-nonproducing BrdUrd-inducible (PRL⁻) rat pituitary tumor cell line. Such cell lines can be obtained by growing rat pituitary tumor cells in gradually increasing concentrations of BrdUrd, using the general technique described by Biswas et al. (1977) Cell 11:431–439. Specifically, suitable PRL⁻ cell lines ($GH_12C_1$) can be obtained from rat pituitary tumors, and then subjected to gradually increasing doses of BrdUrd to yield a more resistant strain (e.g. $F_1BGH_12C_1$). A specific starting cell line that could be used for such a procedure is $GH_3$ (ATCC CCL 82.1).

High molecular weight DNA from such cell lines (designated, e.g., $GH_3/F_1BGH_12C_1$)) is obtained by the general method of Gross-Ballard (1973) J. Biochem. 36:32. That DNA is digested with EcoRI, and the fragments are separated on a 1 percent low-melting agarose gel. The 11-kb fragments of the genomic DNA are extracted from the gel and cloned in an EcoRI site of a suitable vehicle such as the λ Charon 4A described in Blattner et al. (1977) Science 196:161, yielding "λ104".

The 11.2 kb 5′ end rPRL DNA sequences accordingly represent the specific region of the BrdUrd-inducible PRL gene in transformed rat pituitary cells (λ104). The 11.2 kb EcoRI DNA fragment isolated from λ104 is digested with restriction endonuclease BamH1, which generates two DNA fragments (0.9 kb and 10.3 kb). These are separated by low melt agarose (1 percent) gel electrophoresis and extraction as described above. The amplicon is contained within the 10.3 kb segment.

C. The hGH gene

The hGH gene sequence is recovered using similar techniques from the plasmid hGH pBR322 described by DeNote et al. (1981) Nucleic Acid Research 9:3719–3730.

D. Assembling the Hybrid DNA

The 10.3-5′ rPRL gene sequence is ligated to HSV1Tk and hGH DNA sequences using standard recombinant DNA techniques. The hybrid DNA (16.4 kb) is separated from the rest of unreacted DNA fragments by electrophoresis on a low melt agarose gel, and the high molecular weight DNA is extracted from agarose and characterized by Southern blot analysis.

In FIG. 1, the top sketch shows the amplified (solid area) and unamplified (open area) regions of the PRL gene and its neighboring sequences in BrdUrd-treated cells. The second sketch from the top shows the organization of rPRL gene. Solid blocks are exons and the regions designated by letters A to D are the introns in the rPRL gene. The last sketch shows the organization of the "Hybrid DNA". The numbers under HSV1Tk, hGH and the Hybrid DNA designate the length (kilobases) of the specific DNA sequence. The arrows show the recognition sites of the indicated restriction endonucleases.

The hybrid DNA can be characterized by Southern blot analysis. The DNA is separated according to its electrophoretic mobility and the identity of fragments thus separated is verified by radiolabeled hybridization probes.

III. Transfer of Hybrid DNA into Mouse Cells

The transfer of the HSV1Tk-10.3-5′ rPRL-hGH hybrid DNA into Tk⁻ mouse L cells is executed according to the method of Wigler et al. (1977) Cell 11:223–232. The selection of the transfectants is carried out on the basis of the transfer of HSV1Tk gene as indicated by the HAT-resistant [Szybalska et al. (1962) Proc. Nat'l. Acad. Sci. (USA) 48:2026–2048] phenotype of the cells (Table-1). About 25–32 HAT resistant transfectants per $10^6$ recipient cells are obtained in these series of transfections. Transfer of the sequences of the hybrid DNA into the mouse cell is verified by dot hybridization analysis of transfectant DNA as described by Wilson et al. (1983) cited above.

Transfectants retain the original orientation of the hybrid DNA (5′ to 3′): HSV1Tk-rPRL 10.3-5′ rPRL-hGH, as can be demonstrated by Xba I digestion to generate three fragments of about 3.8 kb, 6.6 kb, and 9.4 kb respectively. The latter fragment hybridizes to the $^{32}$P-labeled HSV1Tk and the 6.6 kb fragment hybridizes with $^{32}$P-labeled hGH DNA. The smaller fragment does not hybridize with either probe. These results suggest that the HSV1Tk DNA is still attached to the 5′ end of the 10.3 kb DNA in the transfectant chromosone. The 6.6 kb fragment is composed of 2.7 kb×ba I fragment of rPRL 10.3 kb and 2.6 kb hGH DNA, demonstrating that the 3′ end structure of the 10.3 kb rPRL DNA is attached to the hGH DNA.

IV. Amplification of the Hybrid DNA Sequence in Transfectants

The levels of hybrid DNA sequences in control and BrdUrd treated transfectants are examined to demonstrate amplification of the hybrid specific sequences in these cells. The transfectants are found to be sensitive to BrdUrd and to grow only on concentrations of the drug lower than 10 µg/ml.

To study the BrdUrd-induced amplification of specific DNA sequences, the transfectants are grown in the presence of 10 µg/ml of the drug for 7–10 days. Results of dot hybridization analysis of the DNA isolated from control and drug treated cells show that levels of HSV1Tk and rPRL-10.3 kb DNA sequences are higher in equal amounts of BrdUrd-treated cell DNA of transfectants carrying the 10.3 kb DNA fragment (λ104) from BrdUrd-inducible cells. BrdUrd treatment of the transfectants carrying control DNA [i.e., 10.3 kb fragment from non-inducible PRL+ GH cells] does not affect the level of either HSV1Tk or rPRL 10.3 kb sequences in the transfectants.

Similarly the levels of hGH sequence in one of the transfectants of each series is determined after treatment of the cells with BrdUrd (10 µg/ml, 7d). Dot hybridization analysis of the transfectant DNA again reveals that the [$^{32}$P]hGH-hybridizable sequence is significantly greater in the drug-treated transfectant which carries the hybrid DNA with 10.3 kb from BrdUrd-inducible cells, whereas the BrdUrd treatment does not affect the levels of hGH sequence in transformants with control DNA.

The amplification of the hybrid DNA sequence in the transfectants carrying the 10.3 kb from BrdUrd-inducible cells is further verified by Southern blot analysis of the transfectant cell DNA. DNA from untreated and BrdUrd-treated inducible transfectants is digested with Xba I and the fractioned DNA is hybridized with $^{32}$P-labelled 11.2 kb DNA sequence. The levels of all three Xba I fragments of the hybrid DNA are greater in BrdUrd treated cells. These results further substantiate that the hybrid DNA sequences, including HSV1Tk and hGH sequences, are all amplified following treatment of the cells with BrdUrd. More specifically, in order to demonstrate amplification, the levels of specific regions of hybrid DNA sequence in transfectants are determined using dot hybridization and labeled probes as described by Wilson et al. (1983) DNA 2:237–242.

Without being bound to any particular theory, it appears that the above-described gene amplification is different from previously recognized gene amplification phenomena such as: (1) amplification of genes that occurs during normal developmental processes, such as amplification of rRNA genes during oogenesis as reported by Brown et al. (1968) Science(160:272–280); or (2) the stable and permanent acquisition of a trait such as toxin resistance.

Amplification is limited to 20 kb length of DNA in the neighborhood of rat PRL gene sequences in GH cells, and this DNA sequence is flanked by unamplified sequences at both ends thus designating a unit of amplification. The DNA sequence effecting the BrdUrd-inducible gene amplification is located in 10.3 kb 5' end rPRL gene sequence. Transfectants carrying this DNA segment from the BrdUrd-inducible cells induces amplification of both the 3' and 5' end neighbouring sequences.

PRL gene amplification observed in this GH cell strain in response to the drug BrdUrd is a true induction phenomenon. The onset and the termination of the phenomenon can be controlled by an externally administered agent.

Other embodiments are within the following claims.

I claim:

1. Hybrid DNA capable of effecting the amplification in a host cell of a heterologous gene determining a desired function, said hybrid DNA comprising two regions:
   (1) a first DNA region comprising an amplicon inducible by 5-bromodeoxyuridine, said amplicon being a segment from the 10.3 kb rat prolactin amplicon-containing fragment of ATCC deposit 40187, and
   (2) a second DNA region adjacent to said first DNA region comprising said heterologous gene,
   said hybrid DNA being capable of amplifying the number of copies of said heterologous gene in a host cell transformed with said hybrid DNA responsive to 5-bromodeoxyuridine.

2. The hybrid DNA of claim 1 further comprising a selectable marker wherein said selectable marker is a thymidine kinase gene.

3. The hybrid DNA of claim 2 further comprising a selectable marker wherein said selectable marker gene encodes resistance to an antibiotic.

4. The hybrid DNA of claim 1 wherein said heterologous gene codes for human growth hormone.

5. A cell comprising the hybrid DNA of claim 1.

6. The cell of claim 5 wherein said cell is a eucaryotic cell.

7. The cell of claim 6 wherein said eucaryotic cell is a mammalian cell.

8. A method of producing a desired compound comprising,
   introducing into a host cell hybrid DNA capable of effecting the amplification in a host cell of a heterologous gene determining a desired function said hybrid DNA comprising two regions:
   (1) a first DNA region comprising an amplicon inducible by 5-bromodeoxyuridine, said amplicon being a segment from the 10.3 kb rat prolactin amplicon-containing fragment of ATCC deposit 40187, and
   (2) a second DNA region adjacent to said first DNA region comprising said heterologous gene,
   said hybrid DNA being capable of amplifying the number of copies of said heterologous gene in a host cell transformed with said hybrid DNA responsive to 5-bromodeoxyuridine,
   growing said host cells with said hybrid DNA to a desired population,
   changing an external stimulus to effect amplification of said heterologous gene in the members of said population,
   culturing cells in which said gene is amplified, and recovering said compound.

9. The method of claim 8 wherein said host cell is a eukaryote.

10. The method of claim 9 wherein said host encaryotic cell is a mammalian cell.

11. The method of claim 8 wherein said compound is human growth hormone.

* * * * *

UNITED STATES PATENT AND TRADEMARK OFFICE
CERTIFICATE OF CORRECTION

PATENT NO. : 4,766,067

DATED : August 23, 1988

INVENTOR(S) : Debajit K. Biswas

It is certified that error appears in the above-identified patent and that said Letters Patent is hereby corrected as shown below:

Column 1, line 67, "thymidine" is misspelled;

Column 2, line 64, "segment" is misspelled;

Column 3, line 36, "Enquist" is misspelled;

Column 6, claim 3, line 27, "claim 2" should be --claim 1--.

Signed and Sealed this

Twentieth Day of December, 1988

Attest:

DONALD J. QUIGG

*Attesting Officer*  *Commissioner of Patents and Trademarks*